United States Patent [19]

Ohshima et al.

[11] Patent Number: 5,609,609
[45] Date of Patent: Mar. 11, 1997

[54] SURGICAL SUTURE AND METHOD FOR PREPARATION THEREOF

[75] Inventors: Hiroshi Ohshima; Satoshi Hashimoto, both of Ayabe, Japan

[73] Assignee: Gunze Limited, Ayabe, Japan

[21] Appl. No.: 587,453

[22] Filed: Dec. 21, 1995

[30] Foreign Application Priority Data

Dec. 28, 1994 [JP] Japan .................................. 6-327846

[51] Int. Cl.$^6$ .................................. A61B 17/04
[52] U.S. Cl. .................................. 606/231
[58] Field of Search .................................. 606/228–231

[56] References Cited

U.S. PATENT DOCUMENTS

| | | | |
|---|---|---|---|
| 4,185,637 | 1/1980 | Mattel | 606/230 |
| 4,201,216 | 5/1980 | Mattel | 606/230 |
| 4,532,929 | 8/1985 | Matei et al. | 606/230 |
| 4,844,067 | 7/1989 | Ikada et al. | 606/231 |
| 4,983,180 | 1/1991 | Kawai et al. | 606/230 |

*Primary Examiner*—Michael Powell Buiz
*Assistant Examiner*—Nancy Connolly Mulcare
*Attorney, Agent, or Firm*—Hardaway Law Firm, PA

[57] ABSTRACT

The invention provides a surgical suture comprising a suture body and a coating layer comprising ingredients A, B and C:

<ingredient A> at least one higher fatty acid salt;

<ingredient B> at least one film-forming polymer selected from the group consisting of polycaprolactone, caprolactone-lactic acid copolymer, caprolactone-glycolic acid copolymer, polylactic acid and lactic acid-glycolic acid copolymer; and <ingredient C> at least one sucrose fatty acid ester; and method for preparation thereof.

12 Claims, No Drawings

SURGICAL SUTURE AND METHOD FOR PREPARATION THEREOF

FIELD OF THE INVENTION

The present invention relates to surgical sutures and methods for preparation thereof.

BACKGROUND ART

Surgical sutures are requested to have properties of nontoxicity, appropriate smoothness, high knot strength, etc. In order to impart the properties to surgical sutures, proposed are sutures prepared by coating suture bodies consisting of bioabsorbable polymers such as homopolymer or copolymer of lactide, glycolide, etc., with higher fatty acid salts (U.S. Pat. No. 4,532,929); compositions comprising higher fatty acid salts and film-forming polymers, such as poly(p-dioxanone), polycaprolactone and polyethyleneoxide (U.S. Pat. Nos. 4,201,216; 4,624,256; 5,378,540; and 5,380,780); sucrose fatty acid esters (U.S. Pat. No. 4,844,067).

When only higher fatty acid salts are attached to suture bodies, however, a problem of easy strip of coating layer arises. Although sutures coated with compositions comprising higher fatty acid salts and film-forming polymers, such as poly(p-dioxanone), polycaprolactone and polyethyleneoxide, have improved lubricating properties, said sutures have a problem of decreased knot strength. Sutures coated with sucrose fatty acid esters are fair in properties of smoothness and knot strength. However, said sutures are requested to have further improved properties.

Maintenance of knot strength of sutures becomes difficult in proportional to improvement of smoothness of sutures leading to higher slip properties thereof.

It is an object of the invention to provide surgical sutures having outstanding properties in both smoothness and knot strength without toxicity.

DISCLOSURE OF THE INVENTION

The inventors conducted extensive research in consideration of said problems of prior art, and found that smoothness and knot strength of sutures are further improved by forming a coating layer comprising higher fatty acid salts and film-forming polymers and further comprising sucrose fatty acid esters.

Thus, the invention provides the following surgical sutures and methods for preparing thereof.

1. A surgical suture comprising a suture body and a coating layer comprising ingredients A, B and C:

<ingredient A> at least one higher fatty acid salt;

<ingredient B> at least one film-forming polymer selected from the group consisting of polycaprolactone (hereinafter referred to as "PCL"), caprolactone-lactic acid copolymer (hereinafter referred to as "P-CL/LA"), caprolactone-glycolic acid copolymer (hereinafter referred to as "P-CL/GA"), polylactic acid (hereinafter referred to as "PLA") and lactic acid-glycolic acid copolymer (hereinafter referred to as "P-LA/GA"); and <ingredient C> at least one sucrose fatty acid ester. (hereinafter referred to as "first invention")

2. A surgical suture comprising a suture body, a first coating layer comprising ingredients A and B, and a second coating layer comprising ingredient C:

<ingredient A> at least one higher fatty acid salt;

<ingredient B> at least one film-forming polymer selected from the group consisting of PCL, P-CL/LA, P-CL/GA, PLA and P-LA/GA; and <ingredient C> at least one sucrose fatty acid ester. (hereinafter referred to as "second invention")

3. A method for preparing a surgical suture comprising (i) dissolving or dispersing in a solvent a composition which comprises at least one higher fatty acid salt and at least one film-forming polymer selected from the group consisting of PCL, P-CL/LA, P-CL/GA, PLA and P-LA/GA and at least one sucrose fatty acid ester; and (ii) making to adhere said composition to said suture body to form a coating layer. (a method for producing a surgical suture of first invention).

4. A method for preparing a surgical suture comprising steps of:

(i) forming a first coating layer by dissolving or dispersing a composition which comprises at least one higher fatty acid salt and at least one film-forming polymer selected from the group consisting of PCL, P-CL/LA, P-CL/GA, PLA and P-LA/GA, followed by making to adhere said composition to said suture body; and (ii) forming a second coating layer by making to adhere said sucrose fatty acid ester to said suture with a first coating layer obtained by the step (i). (a method for producing a surgical suture of second invention).

With respect to first invention

The first invention is described below in detail.

Examples of higher fatty acids of higher fatty acid salts employed as ingredient A are $C_{10}$–$C_{30}$ fatty acids, preferably $C_{12}$–$C_{22}$ fatty acids, more preferably $C_{12}$–$C_{18}$ fatty acids. Said higher fatty acids are saturated or unsaturated, and may be branched.

Specifically, said higher fatty acids include lauric acid, myristic acid, palmitic acid, stearic acid, oleic acid, palmitoleic acid, eicosanoic acid and docosanoic acid, preferably include lauric acid, myristic acids palmitic acid and stearic acid.

Examples of salt of higher fatty acid salts are sodium, potassium and like alkali metal salts, calcium, magnesium and like alkaline earth metal salts, preferably calcium and magnesium salts, more preferably calcium salt.

Calcium stearate is a particularly preferable higher fatty acid salt as ingredient A.

Ingredient B comprises at least one film-forming polymer selected from the group consisting of PCL, P-CL/LA, P-CL/GA, PLA and P-LA/GA. Preferable film-forming polymer include PCL, PLA and P-CL/LA.

Ingredient C comprises at least one sucrose fatty acid ester. Said sucrose fatty acid esters have 1–8 fatty acid or acids, preferably 2–8 fatty acids linked with sucrose by an ester bond. Fatty acids linked with sucrose are not specifically limited to, but include $C_2$–$C_{22}$ fatty acids. Said fatty acid esters are esters linked with one type of fatty acid or mixed ester linked with 2 or more types of fatty acids. Preferable fatty acids include stearic acid, palmitic acid, lauric acid and myristic acid.

An amount of said coating layer comprising ingredients A B and C is about 0.5–10% by weight, preferably about 2–5% by weight when taking an amount of the suture body as 100% by weight. The amount of said coating layer ranging about 2–5% by weight leads to improved smoothness, inhibition of strip of said coating layer in the form of powder and maintenance of knot strength of suture substantially as high as knot strength of the suture body, thereby preferable.

The surgical suture of the first invention comprising said coating layer and said suture body includes sutures, inside of which said composition enters and adheres to, besides said coating layer is formed outside of said suture body. Therefore, said weight of coating layer means a total weight of inside and outside of the suture body.

Conventional sutures may be employed as the suture body of the invention. Materials thereof include bioabsorbable materials such as polyglycolic acid and glycolic acid-lactic acid copolymer, silk, polyester and complex thereof, preferably include polyglycolic acid. Said suture body is prepared in the form of monofilament, braid, twisted yarn, etc., preferably braid. A particularly preferable suture body is a braid suture made of bioabsorbable polymer.

Said surgical sutures of the first invention and second invention may be prepared by forming a coating layer on monofilament or multifilament, followed by braiding monofilament or multifilament covered by said coating layer. Said surgical sutures may also be prepared by forming coating layer on multifilament having a braid structure. The surgical sutures of the invention include both of them.

A proportion of ingredients A, B and C preferably meets the condition of A>C≧B.

Preferable concentrations of each ingredient in a solvent are about 5–8% by weight (ingredient A); about 0.5–2% by weight (ingredient B); and about 1–3% by weight (ingredient C).

The amounts of said ingredients contained in the surgical suture are:

Ingredient A=about 1.0–3.5% by weight;

Ingredient B=about 0.1–0.5% by weight; and

Ingredient C=about 0.3–1.5% by weight;

The surgical suture of the first invention include the following suture further having an outer layer comprising ingredient B or ingredient C.

* a surgical suture composed of a suture body, a coating layer I comprising ingredients A, B and C, and a coating layer II comprising ingredient B (ingredients A, B and C are as defined above).

* a surgical suture composed of a suture body, a coating layer I comprising ingredients A, B and C, and a coating layer II' comprising ingredient C (ingredients A, B and C are as defined above).

With respect to said surgical suture having two coating layers, a weight ratio of the coating layer I to the coating layer II; and a weight ratio of the coating layer I to the coating layer II' are the same as a weight ratio of the second invention below. A weight ratio of ingredients A, B and C of said coating layer I is as defined above.

The surgical suture of the first invention may be produced by dissolving or dispersing in a solvent a composition comprising ingredients A, B and C, followed by making to adhere said composition to a suture body. Examples of the solvent used in said method are ethanol, isopropanol and like alcohols, dichloromethane, chloroform and like halogenated hydrocarbons, acetone, methylethylketone and like ketones, ethyl acetate and like esters, which are used individually or in a mixture of two or more.

Adhesion of said composition to the suture body so as to form a coating layer is usually carried out by dipping a suture body in the solution or dispersion of said composition, followed by drying the solvent. Adhesion may also be carried out by spraying or coating said solution or dispersion to the suture body, followed by drying the solvent.

The coating layer of first invention may include a variety of additives other than ingredients A, B and C. Said additives include antibiotics, colorants, etc.

With respect to second invention

Ingredients A, B and C are the same as those of the first invention.

The amount of first coating layer ranges about 0.5–8.0% by weight, preferably about 1.5–4.0% by weight when taking an amount of suture body as 100% by weight.

The amount of second coating layer ranges about 0.1–2.0% by weight, preferably about 0.3–1.5% by weight when taking an amount of suture body as 100% by weight.

The borderline of first coating layer and second coating layer may be clearly formed. Alternatively, a borderline region may be formed by a mixture of ingredients A, B of first coating layer and ingredient C of second coating layer. In this case, outer surface of second coating layer is occupied by ingredient C.

Therefore, the first coating layer means a coating layer whose major components are ingredients A and B, and the second coating layer means a coating layer whose major component is ingredient C.

The surgical suture of second invention may be prepared by steps of (i) dissolving or dispersing in a solvent a composition of ingredients A and B, followed by making to adhere said composition to suture body so as to form the first coating layer; and (ii) dissolving in a solvent ingredient C, followed by making to adhere ingredient C to said first coating layer so as to form the second coating layer according to the procedure of the first invention.

The solvent dissolving or dispersing ingredients A and B, and the solvent dissolving ingredient C are as defined above.

When hexane, benzene and like solvents which are difficult to dissolve ingredients A and B are employed as the solvent of ingredient C, the borderline of first coating layer and second coating layer become clear.

The coating layers may contain antibiotics, colorants, etc.

According to the invention, surgical sutures having the properties of nontoxicity, strong knot strength, outstanding smoothness and least strip of powder of treating agents coated are provided.

EXAMPLE

The present invention will be described below in detail with examples and comparative examples.

EXAMPLE 1

Surgical sutures of the invention was produced according to the following materials and methods.

(1) Material

Suture body: a suture to the specifications of USP1-0 prepared by spinning and drawing polyglycolic acid having an intrinsic viscosity of 1.4, followed by braiding the yarn thus obtained.

Ingredient A: Calcium stearate

Ingredient B: polycaprolactone (molecular weight=250,000)

Ingredient C: sucrose fatty acid ester (DK ester F-A10E; DAIICHI PHARMACEUTICAL INDUSTRIES Co., Ltd.)

(2) Method

Calcium stearate, polycaprolactone and sucrose fatty acid ester were dissolved in dichloromethane at concentrations of 6% by weight, 1% by weight and 2% by weight, respectively, so as to prepare a mixed solution of ingredients A, B and C. The suture body was dipped in said solution and dried at 70° C. to obtain a surgical suture. The amount of the coating layer was 2.5% by weight based on the amount of suture body (100% by weight).

EXAMPLE 2

(Step 1)

Calcium stearate and polycaprolactone were dissolved in dichloromethane at concentrations of 6% by weight and 1% by weight, respectively, so as to prepare a mixed solution of ingredients A and B. The suture body was dipped in said solution and dried at 70° C. to form a first coating layer.

(Step 2)

Sucrose fatty acid ester was dissolved in isopropanol at a concentration of 2% by weight. The suture with the first coating layer was dipped in the solution and dried at 80° C. to form the second coating layer.

The amount of the first coating layer was 2.2% by weight and the amount of the second coating layer was 0.5% by weight based on the amount of the suture body (100% by weight).

Comparative Example 1

A surgical suture with a coating layer consisting of calcium stearate (ingredient A) was obtained in the same procedure as in example 1 except that a dispersant of calcium stearate in dichloromethane at a concentration of 6% by weight was used.

The amount of the ingredient A adhered to the suture body was 3% by weight based on the amount of the suture body (100% by weight).

Comparative Example 2

A surgical suture with a coating layer consisting of sucrose fatty acid ester (ingredient C) was obtained in the same procedure as in example 1 except that a solution of sucrose fatty acid ester in isopropanol at a concentration of 2% by weight was used.

The amount of the ingredient C adhered to the suture body was 0.7% by weight based on the amount of the suture body (100% by weight). Comparative Example 3

A surgical suture with a coating layer consisting of ingredients A and B was obtained by carrying out the (step 1) in example 2. The total amount of the ingredients A and B adhered to the suture body was 2.2% by weight based on the amount of the suture body (100% by weight).

<Evaluation Tests>

The sutures obtained in examples 1–2 and comparative examples 1–3 were evaluated in smoothness, existence or absence of powder strip of coating layer and knot strength.

(1) Smoothness (1-1) Dry condition

Dried suture with coating layer and suture body were placed around thigh of five subjects and tied to evaluate smoothness based on the following criteria.

(1-2) Wet condition

Because blood, body fluid etc., were attached to a suture during operation, wet suture was evaluated as a model under operation conditions.

Smoothness of wet suture with coating layer and wet suture body prepared by contact with water was evaluated in the same procedure as above.

Criteria of smoothness

"o": tie down smoothly

"Δ": tie down with squeak

"x": discontinuous movement with skips (2) Powder strip

Powder strip caused by separation of a coating layer was simultaneously evaluated during said smoothness test under dry condition based on the following criteria.

"o": no powder strip occurred

"Δ": a small amount of powder was stripped

"x": powder was scattered around (3) Knot pull strength

Knot pull strength of suture with coating layer and suture body was determined according to USP (United States Pharmacopoeia) XXI (21).

Specifically, breaking strength of suture tested was measured as knot pull strength by tying an elastic rubber tube having an inner diameter of 6.5 mm and a thickness of 1.6 mm with suture to form surgeon's knot, followed by drawing said suture at a pulling rate of 100 mm/min.

Knot pull strength was evaluated based on the following criteria.

"o": 95% or more of knot pull strength of suture body

"Δ": 90–94% of knot pull strength of suture body

"x": 89% or less of knot pull strength of suture body

TABLE 1

<Evaluation Tests>

| Sample | Smoothness Dry | Smoothness Wet | Powder Strip | Knot pull Strength (gf) Determination | Evaluation |
|---|---|---|---|---|---|
| Suture body (Untreated) | x | x | — | 4780 (100%) | o |
| Example 1 | o | o | Δ or o | 4610 (96.4%) | o |
| Example 2 | o | o | o | 4580 (95.8%) | o |
| Comparative Example 1 (A) | o | Δ | x | 4550 (95.2%) | o |
| Comparative Example 2 (C) | Δ | Δ | o | 4370 (91.4%) | Δ |
| Comparative Example 3 (A + B) | o | o | o | 4070 (85.1%) | x |

What we claimed is:

1. A surgical suture comprising a suture body and a coating layer comprising ingredients A, B and C:

<ingredient A> at least one higher fatty acid salt;

<ingredient B> at least one film-forming polymer selected from the group consisting of polycaprolactone, caprolactone-lactic acid copolymer, caprolactone-glycolic acid copolymer, polylactic acid and lactic acid-glycolic acid copolymer; and <ingredient C> at least one sucrose fatty acid ester.

2. A surgical suture according to claim 1 further comprising a coating layer comprising ingredient B as an essential component.

3. A surgical suture according to claim 1 further comprising a coating layer comprising ingredient C as an essential component.

4. A surgical suture according to claim 1 wherein said higher fatty acid salt comprises $C_{12}$–$C_{22}$ fatty acid.

5. A surgical suture according to claim 4 wherein said higher fatty acid salt is calcium stearate.

6. A surgical suture according to claim 1 wherein a proportion of ingredients A, B and C meets the condition of $A > C \geq B$.

7. A surgical suture according to claim 1 wherein an amount of said coating layer is about 2–5% by weight when taking an amount of the suture body as 100% by weight.

8. A surgical suture according to claim 1 wherein said suture body is an absorbable braid suture.

9. A surgical suture according to claim 8 wherein said absorbable braid suture is made of polyglycolic acid.

10. A surgical suture comprising a suture body, a first coating layer comprising ingredients A and B, and a second coating layer comprising ingredient C:

<ingredient A> at least one higher fatty acid salt;

<ingredient B> at least one film-forming polymer selected from the group consisting of polycaprolactone, caprolactone-lactic acid copolymer, caprolactone-glycolic acid copolymer, polylactic acid and lactic acid-glycolic acid copolymer; and <ingredient C> at least one sucrose fatty acid ester.

11. A method for preparing a surgical suture comprising (i) dissolving or dispersing in a solvent a composition which comprises at least one higher fatty acid salt and at least one film-forming polymer selected from the group consisting of polycaprolactone, caprolactone-lactic acid copolymer, caprolactone-glycolic acid copolymer, polylactic acid and lactic acid-glycolic acid copolymer and at least one sucrose fatty acid ester; and (ii) making to adhere said composition to said suture body to form a coating layer.

12. A method for preparing a surgical suture comprising steps of:

(i) forming a first coating layer by dissolving or dispersing a composition which comprises at least one higher fatty acid salt and at least one film-forming polymer selected from the group consisting of polycaprolactone, caprolactone-lactic acid copolymer, caprolactone-glycolic acid copolymer, polylactic acid and lactic acid-glycolic acid copolymer, followed by making to adhere said composition to said suture body; and (ii) forming a second coating layer by making to adhere said sucrose fatty acid ester to said suture with a first coating layer obtained by the step (i).

* * * * *